United States Patent [19] [11] 4,320,068
Schwindt et al. [45] Mar. 16, 1982

[54] PROCESS FOR THE PRODUCTION OF POLYISOCYANATES HAVING A BIURET STRUCTURE

[75] Inventors: Jürgen Schwindt, Leverkusen; Holger Meyborg, Odenthal; Helmut Reiff; Klaus König, both of, Leverkusen, all of Fed. Rep. of Germany

[73] Assignee: Bayer Aktiengesellschaft, Leverkusen, Fed. Rep. of Germany

[21] Appl. No.: 233,736

[22] Filed: Feb. 12, 1981

[30] Foreign Application Priority Data

Feb. 29, 1980 [DE] Fed. Rep. of Germany ....... 3007679

[51] Int. Cl.³ .......................................... C07C 127/24
[52] U.S. Cl. ......................... 260/453 AB; 260/465.1; 260/465.8 R
[58] Field of Search ................................. 260/453 AB

[56] References Cited

U.S. PATENT DOCUMENTS 3,124,605  3/1964  Wagner ..................... 260/453 AB
3,358,010 12/1967  Britain ....................... 260/453 AB

FOREIGN PATENT DOCUMENTS 1043672  9/1966  United Kingdom .

Primary Examiner—Dolph H. Torrence
Attorney, Agent, or Firm—Gene Harsh; Lawrence S. Pope; Thomas W. Roy

[57] ABSTRACT

This invention relates to a new process for the production of polyisocyanates having a biuret structure by reacting aliphatic or cycloaliphatic diisocyanates with sub-stoichiometric quantities of specified aldoximes. When aldoximes are used as the biuretizing agents insoluble ureas are not formed during the reaction and nitriles which are easy to handle and distill are formed as secondary products.

6 Claims, No Drawings

PROCESS FOR THE PRODUCTION OF POLYISOCYANATES HAVING A BIURET STRUCTURE

BACKGROUND OF THE INVENTION

1. Field of the Invention

This invention relates to a new process for the production of polyisocyanates having a biuret structure by reacting aliphatic or cycloaliphatic diisocyanates with sub-stoichiometric quantities of certain aldoximes.

2. Description of the Prior Art

Polyisocyanates having a biuret structure are known. They are obtained, for example, by reacting aromatic or aliphatic polyisocyanates with water, inorganic salts containing water of crystallization or organic compounds containing water of hydration as described in U.S. Pat. No. 3,124,605 or with hydrogen sulphide as described in German Pat. No. 1,165,580, via the intermediate stage of a urea diisocyanate. These known processes have the disadvantage that undesirable, insoluble polyisocyanates containing urea groups are always formed, precipitating as solids and thus blocking, for example, the apparatus used for producing the polyisocyanates containing biuret groups.

It is also known that polyisocyanates having a biuret structure can be obtained by reacting aromatic or aliphatic diisocyanates with monohydric tertiary alcohols as described in U.S. Pat. No. 3,358,010. The disadvantage of this known process lies both in the high reaction temperature required, which is in the range from about 180° to 200° C., and, above all, in the fact that readily inflammable isobutylene gas is formed during the reaction and can only be removed at considerable expense.

New biuretizing agents have now suprisingly been found which makes it possible for high-grade polyisocyanates having a biuret structure to be produced without any of the disadvantages of the known processes. In the context of the invention, the term "biuretizing agent" is used for compounds which react at elevated temperature with organic isocyanates to form compounds containing biuret groups. Thus, water, hydrogen sulphide or tet.-butanol for example are the "biuretizing agents" used in the known processes mentioned above. The new biuretizing agents according to the invention are organic compounds containing aldoxime groups. Where they are used for the production of biuret-group-containing polyisocyanates based on aliphatic or cycloaliphatic diisocyanates, insoluble urea diisocyanates are surprisingly not formed at any stage of the reaction, although the reaction according to the invention is carried out at comparatively low temperatures. In addition, only the nitriles corresponding to the biuretizing agents i.e. substances which are easy to handle and distill, are formed as secondary products apart from readily absorbable carbon dioxide. These nitriles correspond to the residue of the biuretizing agents used, which is inert with respect to the biuretizing reaction.

SUMMARY OF THE INVENTION

The present invention relates to a process for the production of polyisocyanates having a biuret structure, by reacting aliphatic or cycloaliphatic diisocyanates free from biuret groups with substoichiometric quantities of biuretizing agents, characterized in that compounds containing at least one aldoxime group are used as biuretizing agents.

DETAILED DESCRIPTION OF THE INVENTION

Biuretizing agents suitable for use in accordance with the invention are any organic compounds which contain at least one aldoxime group and which are otherwise inert with respect to isocyanate groups. Particularly suitable biuretizing agents according to the invention are compounds corresponding to the following formula

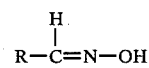

in which R represents a phenyl radical; a linear or branched chain, saturated or unsaturated aliphatic hydrocarbon radical containing from 1 to 6 carbon atoms; a radical corresponding to the following formula

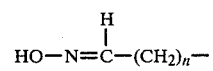

in which n=0 or an integer of from 1 to 5.

Preferred biuretizing agents according to the invention are those compounds corresponding to the above general formula in which R represents a saturated aliphatic, linear or branched chain hydrocarbon radical containing from 1 to 3 carbon atoms or a radical corresponding to the following formula

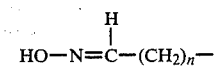

in which n=3 or 4.

Typical examples of suitable biuretizing agents are the oximes and dioximes of benzaldehyde, ethanal, n-propanal, n- and iso-butanal, n-pentanal, n-hexanal acrolein, malonic dialdehyde, succinic dialdehyde, glutaric dialdehyde or adipic dialdehyde. Preferred biuretizing agents are the oximes and dioximes of acetaldehyde, n- and iso-butanal, n-propanal, glutaric dialdehyde or adipic dialdehyde. In a particular embodiment of the process according to the invention, the above-mentioned aldoximes are used in the form of their mixtures with up to about 50 mole percent, preferably from about 10 to 30 mole percent, of water, based on the mixture of biuretizing compounds as a whole. Where mixtures such as these are used, the above-mentioned difficulties observed where water alone is used as biuretizing agent surprisingly do not arise. Any aliphatic or cycloaliphatic diisocyanates are suitable for use in the process according to the invention, compounds corresponding to the following formula

in which Q represents a saturated, aliphatic hydrocarbon radical containing from 2 to 18, preferably 6 to 10, carbon atoms or a cycloaliphatic hydrocarbon radical which may contain alkyl substituents and/or alkylene bridges, and having a total of from 6 to 15, preferably 7 to 13, carbon atoms.

Typical examples of suitable starting diisocyanates are tetramethylene diisocyanate; pentamethylene diisocyanate; hexamethylene diisocyanate; decamethylene diisocyanate; 1,3-cyclopentylene diisocyanate; 1,4-cyclohexylene diisocyanate; 1,2-cyclohexylene diisocyanate; hexahydroxylene diisocyanate; dichlorohexamethylene diisocyanate; 4,4'-dicyclohexyl diisocyanate; 1,2-di-(isocyanatomethyl)-cyclobutane; 1-methyl-2,4-diisocyanato-cyclohexane; 1-methyl-2,6-diisocyanato-cyclohexane; 4,4'-diisocyanato-dicyclohexyl methane; 1,4-diisocyanato-cyclohexane and 1,3-diisocyanato-cyclohexane. Preferred diisocyanates are hexamethylene diisocyanate, the isomeric mixture of 1-methyl-2,4-diisocyanato-cyclohexane and 1-methyl-2,6-diisocyanato-cyclohexane and also 4,4'-diisocyanato-dicyclohexyl methane.

In the practical application of the process according to the invention, at least about 2.5, preferably at least about 3 and, more preferably, from about 6 to 12 moles of the starting diisocyanate are used per gram equivalent of alkdoxime groups present in the biuretizing agent according to the invention. Even where the biuretizing agents used according to the invention are used in admixture with water, these quantitative ratios are preferably maintained between the starting diisocyanate and the aldoximes.

The process according to the invention is generally carried out at temperatures in the range from about 70° to 180° C., preferably at temperatures in the range from about 70° to 160° C., and, more preferably, at temperatures in the range from about 120° to 150° C. The reactants may be premixed at a temperature below this temperature, for example, at room temperature, and then heated to the reaction temperature within the above-mentioned temperature ranges. It is also possible to preheat the starting diisocyanate to a temperature within the above-mentioned temperature ranges and subsequently to add the biuretizing agent. The process according to the invention may also be carried out continuously, for example, in cascades of vessels equipped with stirrers. Depending on the boiling point of the nitrile formed during the reaction, this secondary product is either distilled off continuously during the reaction or is removed from the reaction mixture by distillation after the reaction. Unreacted starting diisocyanate may also be removed in known manner on completion of the reaction, for example using thin-layer evaporators. It is of course, best to use a biuretizing agent which results in a nitrile, the boiling point of which is so different from the boiling point of the starting diisocyanate, that the secondary product may be separated from the excess starting diisocyanate by distillation. The reaction mixture may be worked up after the evolution of carbon dioxide has ceased and, may even be worked up after brief heating to a temperature within the above-mentioned ranges.

There is generally no need for catalysts to be used in the process according to the invention. If desired, acid catalysts, such as boron trifluoride, sulphuric acid, phosphoric acid, phosphorous acid or aluminum trichloride, could be used to accelerate the reaction.

The reaction according to the invention is generally carried out in the absence of solvents, although it may be carried out in an inert solvent, such as dioxane, tetrahydrofuran; triethylene glycol diacetate; toluene, benzene, chlorobenzene, o-dichlorobenzene; butyl acetate; ethylene glycol monoethyl ether acetate or methylene chloride.

Substantially colorless, clear biuret polyisocyanates, i.e., biuret polyisocyanates which are free from insoluble secondary products, are always obtained in the process according to the invention. The products of the process according to the invention are valuable starting materials for the production of polyurethane plastics. They are particularly suitable for use as isocyanate component in two-component polyurethane lacquers.

The process according to the invention is illustrated by the following Examples in which all the percentages quoted represent percent by weight.

EXAMPLE 1

168 g (1 mole) of hexamethylene diisocyanate are introduced into, and heated to 120° C., in a reaction apparatus equipped with a heating jacket, a stirrer, a thermometer, a dropping funnel and an acetone/dry ice cold trap. 9.83 g (0.166 mole) of acetaldoxime are added dropwise at that temperature. This produces an increase in the reaction temperature to 135°–145° C., accompanied by the vigorous evolution of carbon dioxide. The acetonitrile which is distilled off at the same time is collected in the cold trap. The dropwise addition rate is regulated so that the temperature of the reaction mixture does not exceed 145° C. After the aldoxime has been added and the evolution of carbon dioxide has stopped, the reaction mixture is stirred for another 60 minutes at 130° to 135° C. Excess hexamethylene diisocyanate is then separated off from the biuret polyisocyanate formed by thin-layer distillation. 74.8 g of a liquid, clear, substantially colorless biuret polyisocyanate are obtained as the distillation residue. The isocyanate content amounts to 22.8% and the monomer content to 0.67%.

EXAMPLE 2

9.83 g of acetaldoxime are mixed at room temperature with 168 g of hexamethylene diisocyanate in the same apparatus as described in Example 1. The reaction mixture is then heated gradually with stirring. The evolution of carbon dioxide begins at 90° to 100° C. Beyond 120° C., the reaction becomes violent with very intense heat effect. The reaction mixture is maintained at a temperature of 125° to 135° C. by cooling until the evolution of gas has ceased. The acetonitrile escaping from the reaction mixture, together with the carbon dioxide, is condensed in the cold trap. 72.0 g of a liquid, clear, substantially colorless biuret polyisocyanate are obtained as distillation residue after excess hexamethylene diisocyanate has been distilled off in a thin-layer evaporator. The isocyanate content amounts to 22.4% and the monomer content to 0.58%.

EXAMPLE 3

168 g (1 mole) of hexamethylene diisocyanate are introduced into the reaction apparatus described in Example 1 and heated to 130° C. A mixture of 7.37 g (0.125 mole) of acetaldoxime and 0.75 g (0.041 mole) of water is then added dropwise with stirring. After the evolution of carbon dioxide and acetonitrile, which is collected in the cold trap, the excess hexamethylene diisocyanate is removed by distillation in a thin-layer evaporator. 74 g of a liquid, clear, substantially colorless biuret polyisocyanate having an isocyanate content of 23.1% and a monomer content of 0.28% are obtained.

EXAMPLES 4 to 14

Using the apparatus described in Example 1, various diisocyanates are reacted with various biuretizing agents by the method described in Example 1. The experimental details and the results obtained are set out in Table 1 below. After thin layer distillation, the products of the process have monomer contents of less than 0.7%.

TABLE 1

| Example No. | Diisocyanate | Biuretizing Agent |
|---|---|---|
| 4 | 6 moles HDI* | 1 mole propanaldoxime |
| 5 | 6 moles HDI | 0.67 mole propanaldoxime 0.33 mole water |
| 6 | 6 moles HDI | 1 mole butyraldoxime |
| 7 | 6 moles HDI | 0.67 mole butyraldoxime 0.33 mole water |
| 8 | 6 moles HDI | 1 mole isobutyraldoxime |
| 9 | 6 moles HDI | 0.67 mole butyraldoxime 0.33 mole water |
| 10 | 12 moles HDI | 1 mole glutarodialdoxime |
| 11 | 24 moles HDI | 0.85 mole glutarodialdoxime 0.30 mole water |
| 12 | 12 moles HDI | 1 mole adipodialdoxime |
| 13 | 12 moles 4,4'-diisocyanato-dicyclohexyl methane | 1 mole propanaldoxime |
| 14 | 12 moles isomer mixture** | 1 mole propanaldoxime |

| Example No. | Dropwise addition temp. (°C.) | Biuret triisocyanate % NCO | Nitrile |
|---|---|---|---|
| 4 | 135–140 | 23.2 | propionitrile |
| 5 | 135–140 | 22.9 | propionitrile |
| 6 | 140 | 22.7 | n-butyronitrile |
| 7 | 140 | 23.1 | n-butyronitrile |
| 8 | 140 | 23.4 | isobutyronitrile |
| 9 | 140 | 23.4 | isobutyronitrile |
| 10 | 145 | 22.4 | glutaric acid dinitrile |
| 11 | 145 | 22.3 | glutaric acid dinitrile |
| 12 | 145 | 22.8 | adipic acid dinitrile |
| 13 | 140 | 14.8 | propionitrile |
| 14 | 140 | 21.3 | propionitrile |

*hexamethylene diisocyanate
**isomer mixture of 1-methyl-2,4-diisocyanato-cyclohexane and 1-methyl-2,6-diisocyanato-cyclohexane (weight ratio 80:20)

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of polyisocyanates having a biuret structure by reacting aliphatic or cycloaliphatic diisocyanates free from biuret groups with sub-stoichiometric quantities of biuretizing agents, characterized in that compounds containing at least one aldoxime group are used as the biuretizing agent.

2. The process as claimed in claim 1, characterized in that aldoxime corresponding to the following formula

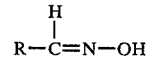

in which R represents a phenyl radical; a linear or branched chain, saturated or unsaturated aliphatic hydrocarbon radical containing from 1 to 6 carbon atoms; or a radical corresponding to the formula

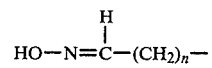

in which n=0 or an integer of from 1 to 5, are used as the biuretizing agent.

3. The process as claimed in claim 1 or 2, characterized in that at least 2.5 moles of diisocyanate are used per gram equivalent of aldoxime groups present in the biuretizing agent.

4. The process as claimed in claim 1 or 2, characterized in that the reaction is carried out at a temperature of from 70° to 180° C.

5. The process as claimed in claim 1 or 2, characterized in that the biuretizing agent is used in the form of a mixture with up to 50 mole percent of water, based on the biuretizing mixture as a whole.

6. The process as claimed in claim 1 characterized in that the oximes of ethanal, n-propanal, n- and iso-butanal or the dioximes of glutaric dialdehyde or adipic dialdehyde are used as the biuretizing agent.

* * * * *